(12) United States Patent
Murphy

(10) Patent No.: US 7,776,098 B2
(45) Date of Patent: Aug. 17, 2010

(54) MODULAR FEMORAL PROSTHESIS WITH ON-AXIS JUNCTION

(76) Inventor: Stephen B. Murphy, 61 Wedgemere Ave., Winchester, MA (US) 01890

( * ) Notice: Subject to any disclaimer, the term of this patent is extended or adjusted under 35 U.S.C. 154(b) by 976 days.

(21) Appl. No.: 11/546,664

(22) Filed: Oct. 12, 2006

(65) Prior Publication Data

US 2008/0091274 A1 Apr. 17, 2008

(51) Int. Cl.
*A61F 2/36* (2006.01)
(52) U.S. Cl. .................. 623/22.42; 623/22.46
(58) Field of Classification Search ............. 623/22.11, 623/22.4–22.46, 23.15–23.38, 23.44–23.46, 623/19.14
See application file for complete search history.

(56) References Cited

U.S. PATENT DOCUMENTS

| 3,938,198 | A |  | 2/1976 | Kahn et al. |
| 4,051,559 | A |  | 10/1977 | Pifferi |
| 4,608,055 | A |  | 8/1986 | Morrey et al. |
| 4,664,668 | A |  | 5/1987 | Beck et al. |
| RE32,488 | E |  | 9/1987 | Gustilo et al. |
| 4,770,661 | A | * | 9/1988 | Oh .......................... 623/22.2 |
| 4,795,469 | A |  | 1/1989 | Oh |
| 4,957,510 | A |  | 9/1990 | Cremascoli |
| 5,100,407 | A |  | 3/1992 | Conrad et al. |
| 5,135,529 | A |  | 8/1992 | Paxson et al. |
| 5,156,624 | A |  | 10/1992 | Barnes |
| 5,286,260 | A |  | 2/1994 | Bolesky et al. |
| 5,405,403 | A |  | 4/1995 | Mikhail |
| 5,413,610 | A |  | 5/1995 | Amino et al. |
| 5,653,764 | A |  | 8/1997 | Murphy |
| 5,653,765 | A |  | 8/1997 | McTighe et al. |
| 6,319,286 | B1 |  | 11/2001 | Fernandez et al. |
| 6,702,854 | B1 |  | 3/2004 | Cheal et al. |
| 2008/0133023 | A1 | * | 6/2008 | Schlotterback et al. .... 623/22.42 |

* cited by examiner

*Primary Examiner*—David H Willse
*Assistant Examiner*—Megan Wolf
(74) *Attorney, Agent, or Firm*—Cesari and McKenna, LLP

(57) ABSTRACT

A modular hip prosthesis includes a femoral stem, a spherical head and a coupling member extending from the head defining a neck whose lower end forms a base which plugs into a socket at the top of the stem to form a tapered neck/stem junction. That junction is aligned with the stem axis and has a cross-section with opposite sides that extend generally parallel to the sides of the stem. With such an arrangement, that junction may be relatively long and have a relatively large cross-sectional area thus making a strong junction even in smaller femoral implants.

5 Claims, 3 Drawing Sheets

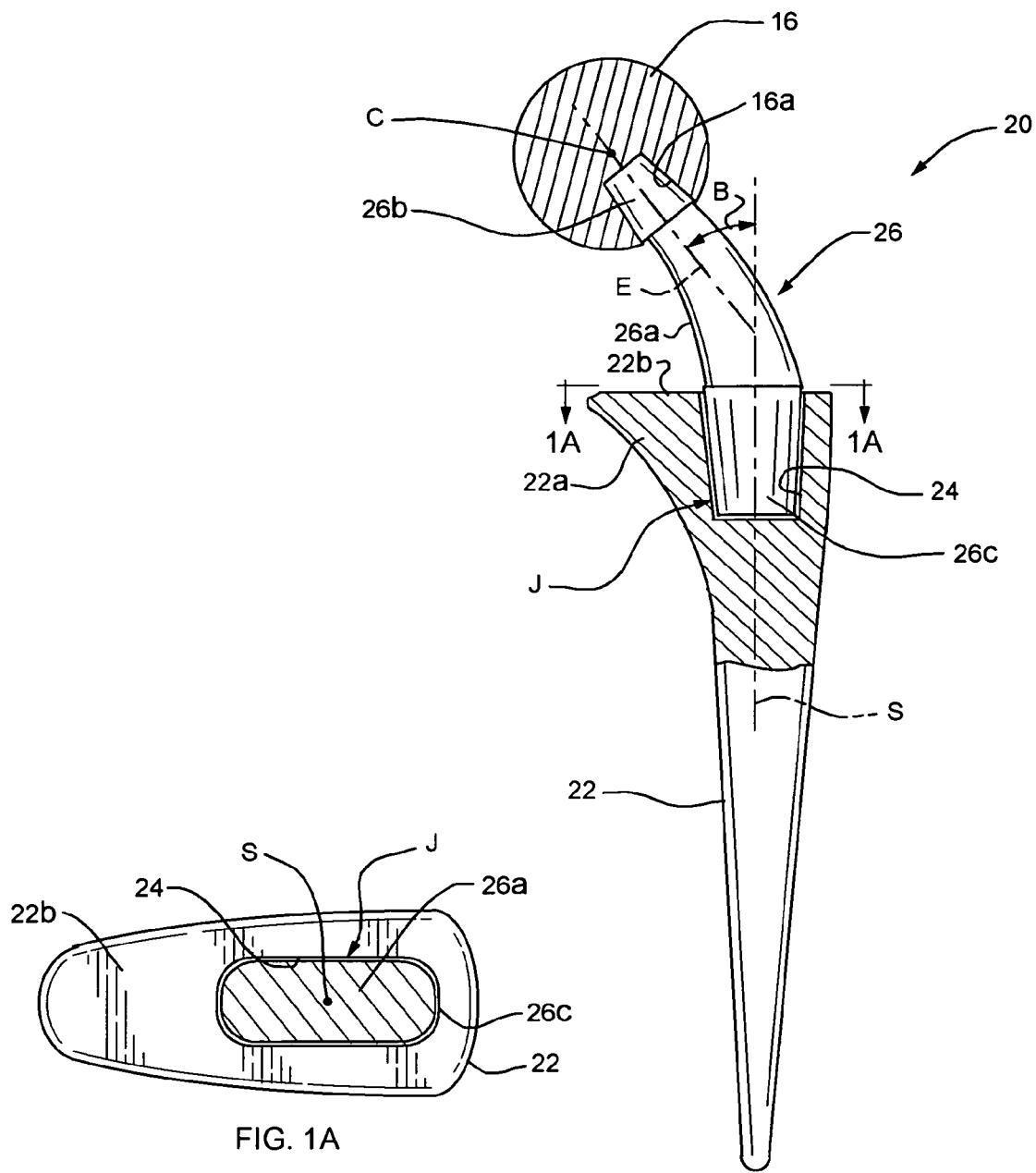
FIG. 1
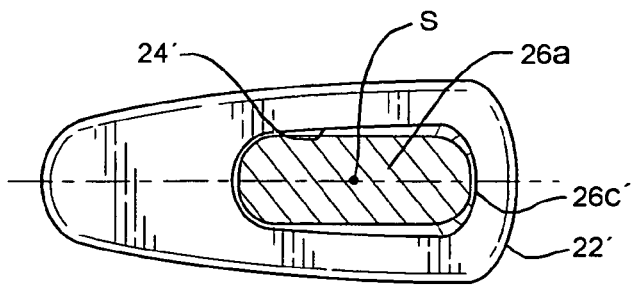
FIG. 1A
FIG. 1B

MODULAR FEMORAL PROSTHESIS WITH ON-AXIS JUNCTION

This invention relates to hip replacements. It relates especially to the femoral component of such a replacement.

BACKGROUND OF THE INVENTION

1. Field of the Invention

Total Hip Arthroplasty (THA) is an effective surgical procedure for the relief of pain and the restoration of function of a diseased hip. Successful THA has contributed to enhanced mobility and comfortable independent living for people who would otherwise be substantially disabled. As shown in FIG. 5, in total hip replacement surgery, the surgeon may replace a patient's diseased hip joint with a conventional implant consisting of a femoral stem 12 which is inserted into the femur and an acetabular cup 14 which is anchored in the patient's pelvis. The upper end of the stem 12 carries a head or ball-type bearing 16. That head seats in a hemispherical socket 14a defined by the cup 14 so that the stem can swivel relative to the cup about the center of curvature of socket 14a in the manner of a natural hip joint.

2. Description of the Prior Art

In a modular femoral prosthesis which is of particular interest here, the head is typically attached to the stem 12 by means of a coupling member 18. Member 18 comprises a straight neck 18a, the upper end of which defines a conical frustum 8b typically a Morse taper, which is wedged into a correspondingly tapered passage 16a in head 16. The lower end or base 18c of neck 18a has an oblong cross-section and is also tapered so it can wedge into a similarly shaped socket 13 in stem 12 as shown in FIG. 5. A hip prosthesis such as this is described in U.S. Pat. No. 4,957,510.

As is typical for such a femoral prostheses, the axis N of the socket 13 in stem 12 is oriented at an angle A with respect to the longitudinal axis S of the stem because the socket extends in from an angled facet 12a in the stem's metaphyseal flare. In other words, the junction J of the neck 18 with the stem 12 is offset from the prosthesis axis S. This offset angle is typically in the order of 45°.

While the prosthesis depicted in FIG. 5 is satisfactory in many respects, it does have certain drawbacks. First, since the neck axis N and neck/stem junction J are oriented at an angle A with respect to the stem axis S, the prosthesis cannot be made in small sizes to suit people with small bones for example, because there would be insufficient metal left in the metaphyseal flare of stem 12 to accommodate the socket 13. In addition, even where there is sufficient metal to accommodate the socket 13, this junction has limited strength that therefore significantly limits the allowable length of the neck 18 that can be used, thus limiting the applicability and safety of the design for patients who have an unusually long native femoral neck that is being replaced. Also, since that junction is placed at an angle to axis S, the vertical distance between the center of rotation of head 16 in acetabular cup 14 and the top of stem 12, and thus leg length, cannot be changed independently of the offset, i.e. the horizontal distance between the center of rotation of head 16 in the acetabulum and the stem axis S, and vice/versa.

In addition, when implanting a femoral stem such as stem 12, the patient's femur must first be subjected to several preliminary procedures. After the femoral canal is prepared and the final trial broach is inserted, a "trial reduction" is typically performed whereby a trial neck and head are affixed to the final trial broach and the femoral trial prosthesis is reduced into the socket to test the hip joint for tissue tension, leg length, range of motion and stability. Given that the socket 13 is at an angle relative to the longitudinal axis of the femoral prosthesis, each assembly and disassembly of the trial neck and assembly of the final prosthetic neck are difficult. The problem is further accentuated by the advent of less invasive surgical techniques where the space within which to accomplish these maneuvers is further reduced.

There do exist femoral prostheses that have generally cylindrical neck/stem junctions that are aligned with the stem axis S. Such an implant is shown in FIG. 6. It comprises a stem 12' having a socket 13' for receiving a neck base 18c both having generally circular cross-sections, thus forming a generally cylindrical neck/stem junction J. While these avoid the aforesaid problems associated with the implants having off-axis junctions, they have inherent drawbacks of their own. More particularly, a simple cylindrical taper junction such as disclosed in U.S. Pat. No. 6,319,256 requires a tight threaded fastener to maintain the junction and is thus potentially rotationally unstable. Another type of known implant strengthens rotational stability by adding teeth or locking pins to the mating surfaces of the neck and stem; see e.g. U.S. Pat. Nos. 5,653,764 and 6,702,854. However, these interfitting surfaces are hard to machine, making those implants difficult and expensive to manufacture.

In addition, those patented prostheses typified by FIG. 6, have a further disadvantage that the metaphysis of the femur is not cylindrical in shape. This means that if the outer dimension of the prosthesis stem is generally not cylindrical in shape but the internal junction J is, then as shown in FIG. 6, the wall thickness of the stem surrounding the junction J varies widely. In particular, the wall of the stem supporting the junction would be thinnest anteriorly and posteriorly. Therefore, the size and strength of a generally cylindrical junction is limited by the minimum wall thickness which, in turn, limits the size and strength of the modular femoral neck that can be associated with the stem.

SUMMARY OF THE INVENTION

Accordingly, the present invention aims to provide an improved modular femoral prosthesis for hip arthroplasty.

Another object is to provide a femoral prosthesis which is rotationally stable, yet relatively easy and inexpensive to manufacture.

Yet another object is to provide a prosthesis of this type which is stronger than conventional implants because it is designed to better match the natural shape of the femur into which it is implanted.

Another object of the invention is to provide such a prosthesis which allows the control or selection of leg length, offset and version as independent variables during the hip arthroplasty.

Yet another object of the invention is to provide a prosthesis of this type which may be sized to suit patients of small stature.

A further object of the invention is to provide a modular hip prosthesis whose design facilitates its implantation during minimally invasive hip arthroplasty.

Other objects will, in part, be obvious and will, in part, appear hereinafter.

The invention according comprises the features of construction, combination of elements and arrangement of parts which will be exemplified in the construction hereinafter set forth, and the scope of the invention will be indicated in the claims.

Briefly, my modular hip prosthesis comprises a femoral stem, a head and a coupling member extending from the head comprising a neck whose lower end defines a base which plugs into a socket at the top of the stem to form a neck/stem junction. However, instead of offsetting the neck/stem junction from the stem axis as depicted in FIG. 5, that junction is substantially aligned with the stem axis.

In addition, rather then providing a generally cylindrical junction as depicted in FIG. 6, the junction in the present implant is relatively long and has a relatively large non-cylindrical cross-section which more closely matches the natural shape of a femur. Thus, there is less variation in the wall thickness of the stem surrounding the socket in the stem. This allows a larger and stronger neck/stem junction to be provided than would be the case with an implant having a cylindrical junction taper. Moreover, my prosthesis is devoid of anti-rotation devices such as teeth, locking pins and threaded fasteners. Therefore, it is easier and less expensive to make than the prior implants requiring such devices.

Also as we shall see, aligning that junction to the stem axis allows for various neck designs that will permit controlling leg length, offset and version independently, and also creates more opportunities for valgus, varus and anteversion implant options.

Finally, in the present prosthesis, since the neck/stem junction is aligned with the stem axis, trial and final necks may be assembled easily to the stem thereby expediting minimally invasive hip arthroplasty.

BRIEF DESCRIPTION OF THE DRAWINGS

For a fuller understanding of the nature and objects of the invention, reference should be made to the following detailed description taken in connection with the accompanying drawings, in which:

FIG. 1 is an elevational view with parts in section showing a femoral prosthesis incorporating the invention comprising a stem component and a separable head component;

FIG. 1A is a sectional view on a larger scale taken along line 1A-1A of FIG. 1;

FIG. 1B is a similar view of another prosthesis embodiment;

DETAILED DESCRIPTION OF ILLUSTRATIVE EMBODIMENTS

Figure 2:
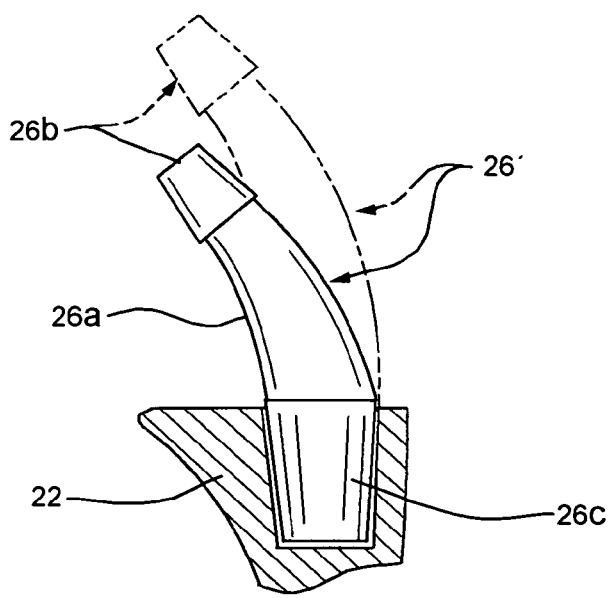
FIG. 2 is a schematic side elevational view showing a range of coupling members for use with the stem in FIGS. 1 to 1B and which provide different leg lengths with the same offset.

Refer now to FIG. 1 of the drawings which shows an embodiment of my improved femoral prosthesis. It comprises a stem 22 having a metaphyseal flare 22a leading up to a flat upper surface 22b which is substantially perpendicular to the stem axis S.

As shown in FIGS. 1 and 1A, a socket 24 extends down into stem 22 from the stem upper surface 22b. Unlike the prior prosthesis depicted in FIG. 5, the socket is centered on the stem axis S and extends in the direction of that axis. Also unlike the prior implant type shown in FIG. 6, the stem socket has a cross-section which is elongated in the direction of the flare 22a. In other words, the socket has sides which extend generally parallel to the sides of stem 22. That being the case, there is more stem material available for the socket 24 in the metaphyseal area 22a of the stem, particularly in the anterior and posterior regions thereof. Accordingly, the socket can be larger and deeper than is the case with the prior prostheses. By the same token, a suitable socket may be formed in relatively small stems 22 suitable for implantation in children and other individuals of small stature.

The implant also includes a conventional spherical head or bearing 16 having a center of curvature C and which is coupled to stem 22 by means of a coupling member indicated generally at 26. The coupling member includes an elongated curved or angled neck 26a whose upper end 26b is connected to head 16. In the illustrated implant, that connection is a standard Morse taper wherein the end 26b is tapered and plugs into a similarly shaped recess 16a in head 16 that is radially aligned with center C. Alternatively, the head and neck may be threadedly connected. Since the head 16 and coupling member 26 are separable, this allows those components to be made of different materials. For example, the coupling member 26 may be of a standard titanium alloy, while the head 16 may be of the same or a different alloy or of a plastic or ceramic material customarily used in hip replacements. Of course, if the head 14 and coupling member 26 are of the same metal alloy, they may be formed as a unitary structure with the head permanently attached to the upper end of the coupling member.

In any event, the lower end segment of neck 26a is shaped to form a tapered base 26c for coupling member 26. That base has substantially the same shape and taper as socket 24 so it can seat snugly in the socket as shown in FIG. 1. In other words, the base 26c also has an elongated cross-section only slightly smaller than the cross-section of socket 24. It may be slightly shorter than the socket so that when the coupling element 26 is seated in stem 22, base 26c wedges into socket 24 thereby firmly, but releasably, anchoring the coupling member to the stem.

As best seen in FIG. 1A, both the socket 24 and the coupling member base 26c have cross-sections that are non-cylindrical thereby creating a neck/stem junction J whose cross-section is similarly non-cylindrical. In the illustrated prosthesis, the junction J has an oblong cross-section. Thus the sides of the junction extend generally parallel to the sides of the stem 22. Therefore, when the coupling member is seated in stem 22, it is rotatably fixed to the stem. Also, it has a preferred angular orientation about the stem axis S, i.e. the neck 26a extends out over the metaphyseal flare 22a as shown in FIG. 1. In order to assure such directionality, the cross-section of the junction J may be made slightly wider at one end of the cross-section than at the other. With such a shape, the coupling member 26 can only be inserted into stem 22 when it is oriented as shown in FIG. 1.

Figure 5:
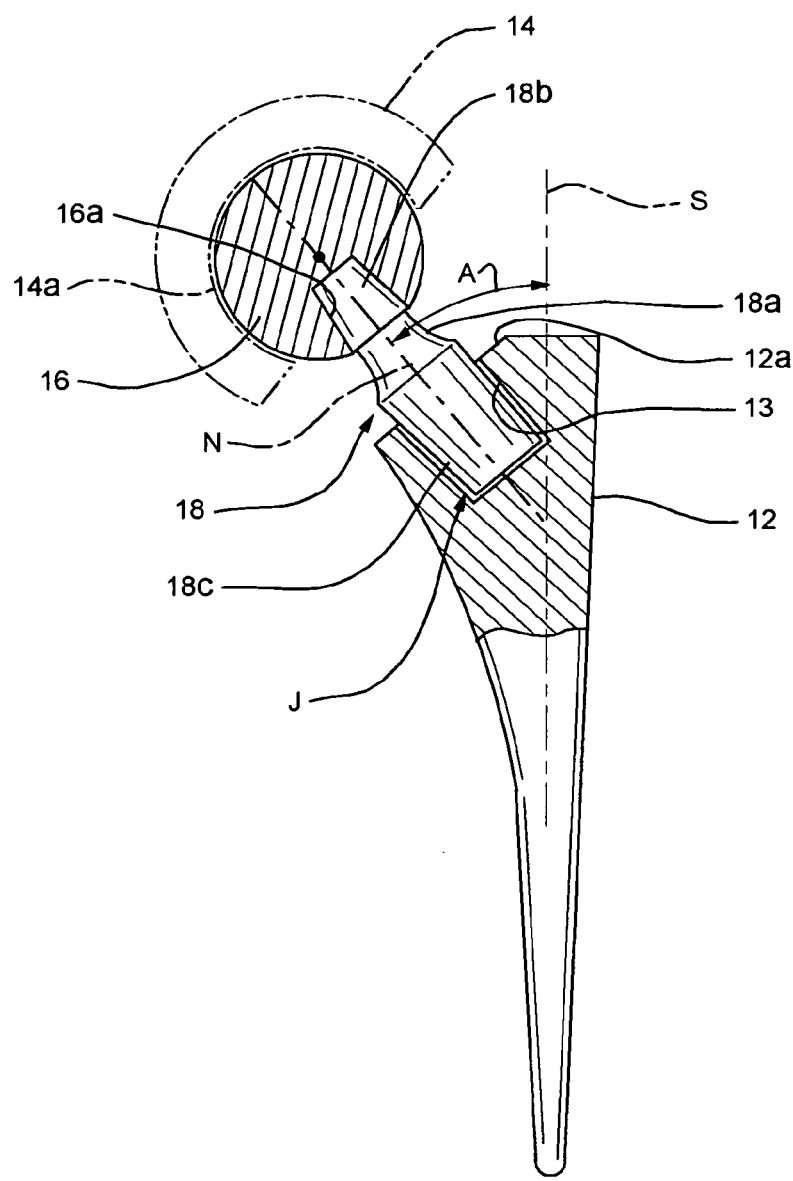
FIG. 5, already described, is an elevational view with parts in section illustrating a total hip implant including a conventional modular femoral prosthesis, and FIG. 6, already described, is a top plan view with parts in section showing another known type of implant.
Figure 6:
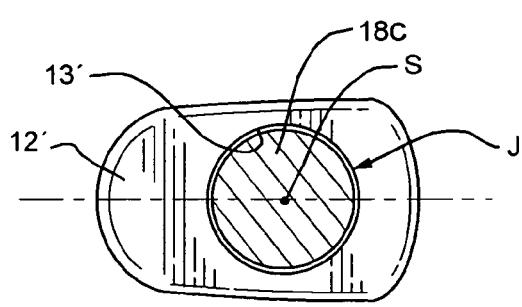

When performing hip arthroplasty, the stem 22 must be implanted in the patient's femur and the head 16 must be rotatably seated in the patient's own acetabulum or in a comparable implanted actetabular cup 14 (FIG. 5). This requires that the neck 26a have a curvature or angulation between base 26c and its upper end 26b which achieves that objective for each individual patient. In other words, a given coupling member 26 must produce a femoral prosthesis which provides the length, the offset and the version/anteversion characteristics which essentially reproduce those of the patient's natural hip joint.

As shown in FIGS. 1 and 1A, the neck 26a of coupling member 26 is angled out over the flare 22a so that the longitudinal axis E of the neck upper end 26b is oriented at an angle B (e.g. 40°-45°) with respect to the axis of the coupling member base 26c which axis corresponds to the stem axis S. In other words, the coupling member 26 has a predetermined length and curvature or angulation which give the overall implant selected overall length, offset and version characteristics to suit a given patient.

It is a feature of my invention that by aligning the neck/stem junction J with the stem axis S, most of the implant variables such as length, offset and version may be controlled independently by proper selection of the coupling member 26. In other words, in the prior prostheses depicted in FIG. 5 whose neck/stem junction J is offset from the stem axis S, any change in the length of the coupling member to change the overall length of the prosthesis would inevitably also change the offset, and vice versa. The present construction decouples those variables.

More particularly, as indicted in FIG. 2, a range of coupling members 26' may be coupled between head 16 and stem 22 to produce a prosthesis which provides the same offset, but different overall lengths.

Figure 3:
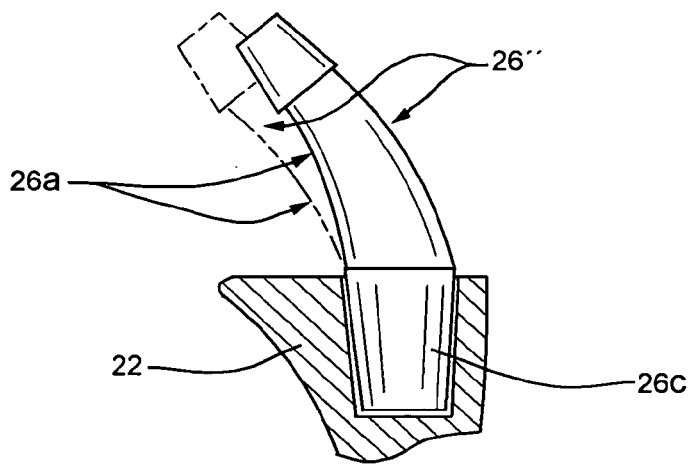
FIG. 3 is a similar view showing a range of such coupling members which provide the same leg length with different offsets.

Likewise, as shown in FIG. 3, the present prosthesis design allows for a range of coupling members 26" which have the same length, but different lateral extents. When coupled between head 16 and stem 22, members 26" will produce a prosthesis that provides the same leg length but different head offsets from the stem axis S.

Figure 4:
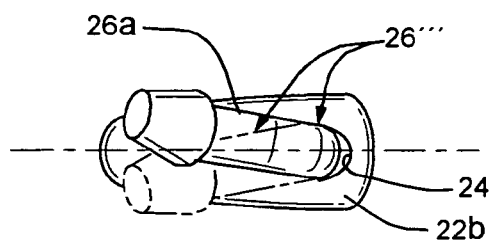
FIG. 4 is a schematic top plan view showing a range of coupling members that achieve different degrees of version/anteversion.

FIG. 4 indicates a range of coupling members 26''' whose necks 26a have a range of twists about the axis B of the coupling member base 26c. By connecting one or another of these coupling members 26''' between head 16 and stem 22, a variety of version/anteversions options are possible depending on the particular patient.

In a similar manner, the necks of 26a of coupling members such as coupling member 26 in FIG. 1 may be shaped to provide a range of vertical deviations from the bend angle B shown there, say between ±/−10°, to provide a range of valgus/varus options.

Refer now to FIG. 1B which depicts the outer shape of the proximal end of many present day femoral implant stems 22'. As shown there, it has the general shape of a trapezoid with rounded corners to more or less match the general shape of the metaphyseal area of a femur. In accordance with this invention, in such a stem, a socket 24' is formed which likewise has the general shape of a trapezoid with rounded corners and which is centered on the stem axis S. In other words, the general shape of the socket should correspond more or less to the shape of the proximal end segment of the stem. This provides a maximum stem wall thickness all around socket 24' so that the cross-sectional area of the neck/stem junction can be a maximum. This means that for a given size stem, the modular neck component of the prosthesis can be larger and stronger than in implants with a cylindrical junction. This is particularly important for implants destined for children and other patients of small stature.

Finally, since the sockets 24, 24' in stems 22, 22' are centered on the stem axis S, those stems can be accessed easily from above when assembling (and disassembling) trial and final modular necks during minimally invasive hip surgery.

It will thus be seen that the objects set forth above, among those made apparent from the preceding description, are efficiently attained. Also, since certain changes may be made in the above constructions without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention described herein.

The invention claimed is:

1. A hip prosthesis comprising
an elongated stem having a longitudinal stem axis and a metaphyseal flare leading up to a flat upper surface extending perpendicular to the stem axis and having opposite, relatively straight sides;
a tapered socket extending a selected distance into the stem from said upper surface, said socket having opposite sides extending substantially parallel to the opposite sides of said surface and being centered on the stem axis;
a substantially spherical head having a center of curvature, and
a coupling member releasably coupling the head to the stem, said coupling member including a neck having a lower end forming a base with a first axis that substantially coincides with the stem axis and an upper end with a second axis and connected to the head so that said second axis extends through said center of curvature and is angularly offset from the first axis, said base also having a length and taper such that it wedgingly engages in the socket to form a releasable, non-rotatable connection therewith which defines a tapered neck/stem junction centered on and aligned with said stem axis and which has a cross-section with opposite ends, one of which is wider than the other and that is elongated in the direction of the metaphyseal flare, said upper surface and cross-section each having the shape of a trapezoid with rounded corners so that the coupling member can only be coupled to the stem when the head is located above the metaphyseal flare.

2. The prosthesis defined in claim 1 wherein the connection between the upper end of the neck and the head is capable of being released.

3. The prosthesis defined in claim 2 wherein the connection between the upper end of the neck and the head comprises a Morse taper.

4. A hip prosthesis comprising an elongated stem having a stem axis and a planar upper surface, said upper surface having opposite, relatively straight sides and extending perpendicular to said axis, and
a tapered socket extending into the stem from said upper surface at said axis, said socket having an elongated mouth with opposite ends one of which is wider than the other and opposite relatively straight sides extending substantially parallel to the opposite sides of said upper surface, said upper surface and said socket mouth each having the shape of a trapezoid with rounded corners.

5. The prosthesis defined in claim 4 and further including a modular neck having a base with substantially the same size and taper as the socket wedgingly received in the socket.

* * * * *